US007550509B2

(12) United States Patent
Roberts et al.

(10) Patent No.: US 7,550,509 B2
(45) Date of Patent: Jun. 23, 2009

(54) CARISOPRODOL ARTICLES AND METHODS

(75) Inventors: Richard H. Roberts, Lakewood, NJ (US); Jie Du, Lansdale, PA (US)

(73) Assignee: Mutual Pharmaceutical Company, Inc., Philadelphia, PA (US)

( * ) Notice: Subject to any disclaimer, the term of this patent is extended or adjusted under 35 U.S.C. 154(b) by 337 days.

(21) Appl. No.: 11/425,175

(22) Filed: Jun. 20, 2006

(65) Prior Publication Data

US 2007/0238779 A1 Oct. 11, 2007

Related U.S. Application Data

(60) Provisional application No. 60/790,202, filed on Apr. 7, 2006.

(51) Int. Cl.
*A61K 31/16* (2006.01)
(52) U.S. Cl. .................................... 514/616
(58) Field of Classification Search .................. 514/616
See application file for complete search history.

(56) References Cited

U.S. PATENT DOCUMENTS 4,536,403 A * 8/1985 Rooks ...................... 514/483
6,761,895 B2 7/2004 Sawada et al.

OTHER PUBLICATIONS

Remington's Pharmaceutical Sciences; Osol et al., published 1980; pp. 1723-1726.*
"Coumadin Tablets"; Physicians' Desk Reference Edition 59; ISBN: 1-56363-497-X; pp. 1039-1044; 2005.
"Soma"; Physicians' Desk Reference Edition 59; ISBN: 1-56363-497-X; p. 1976; 2005.
"Diflucan"; Physicians' Desk Reference Edition 59; ISBN: 1-56363-497-X; pp. 2605-2609; 2005.
"Phenytek Capsules"; Physicians' Desk Reference Edition 59; ISBN: 1-56363-497-X; pp. 2255-2257; 2005.
"Coumadin Tablets"; Prescribing Information; Bristol-Myers Squibb Company; Apr. 2005.
"Meprobamate"; British National Formulary (BNF); ISBN: 0 85369 631 4; p. 180; Mar. 2005.
"Carisoprodol"; British National Formulary (BNF); ISBN: 0 85369 631 4; p. 517; Mar. 2005.
"Carisoprodol"; Healthnotes; http://www.n101.com/HealthNotes/HNs/Drug/Carisoprodol.htm; pp. 1-3; printed Jul. 25, 2005.
"Carisoma Tablets" Summary of Product Characteristics; http://www.forestlabs.com/EthicalProducts/SPC/CarisomaSPC.html; pp. 1-4; printed Aug. 10, 2005.
"Carisoma"; http://www.netdoctor.co.uk/medicines/100003158.html; pp. 1-4; printed Aug. 10, 2005.
"Guidance for Industry Food-Effect Bioavailability and Fed Bioequivalence Studies"; U.S. Department of Health and Human Services, Food and Drug Administration, Center for Drug Evaluation and Research (CDER); pp. 1-10; Dec. 2002.
Tredger; "Cytochromes P450-their impact on drug treatment"; Hospital Pharmacist; 9; pp. 167-173; 2002.
Beardsley, et al. Anticonvulsant Serum Levels are Useful Only if the Physician Appropriately Uses Them: An Assessment of the Impact of Providing Serum Level Data to Physicians Epilepsia, Published 1983, vol. 24, pp. 330-335; Entire document, esp. Summary, p. 330; p. 331, Col 1, paraa 3; pp. 331, Col. 2, para 4.
Poolsup, et al. "Pharmacogenetics and Psychopharmacotherapy", J. Clin. Pharm. Ther. 2000, vol. 25, pp. 197-220.
International Search Report and Written Opinion; International Application No. PCT/US07/21122; International filing date Oct. 1, 2007; Applicant's File No. MPC-0115; Date of Mailing Mar. 10, 2008, 8 pages.
International Search Report dated Dec. 12, 2008 for Application No. PCT/US07/08736.

* cited by examiner

*Primary Examiner*—Raymond J Henley, III
(74) *Attorney, Agent, or Firm*—Cantor Colburn LLP

(57) ABSTRACT

A method of using carisoprodol comprises informing a user that administration of carisoprodol in the presence of food decreases the $C_{max}$ for carisoprodol compared to administration in the absence of food. In one embodiment, informing comprises providing printed labeling instructions. Also included are articles comprising a carisoprodol formulation and prescribing information, and methods of manufacturing carisoprodol dosage forms. Included are measures intended to increase the safe use of narrow therapeutic medications with carisoprodol.

11 Claims, No Drawings

CARISOPRODOL ARTICLES AND METHODS

CROSS REFERENCE TO RELATED APPLICATION

This application claims priority from U.S. Provisional Application Ser. No. 60/790,202 filed Apr. 7, 2006, which is hereby incorporated by reference in its entirety.

BACKGROUND

Carisoprodol, chemical name N-isopropyl-2-methyl-2-propyl-1,3-propanediol dicarbamate, is a pharmaceutical active agent whose metabolite is meprobamate. Metabolism of carisoprodol by cytochrome p450 isoform CYP2C19 has been reported. Carisoprodol was approved by the U.S. FDA on Apr. 9, 1959. It is marketed in the United States under the brand name Soma®, and in the United Kingdom and other countries under the brand name Carisoma®. Carisoprodol is commonly used as a skeletal muscle relaxant.

Carisoprodol is a colorless, crystalline powder, having a mild, characteristic odor and a bitter taste. It is very sparingly soluble in water and freely soluble in alcohol, chloroform, and acetone.

Further in relation to sparingly water soluble drugs, it has been reported that some such drugs are formulated into dosage forms that exhibit improved absorption into the blood stream when administered with food. The plasma concentrations of griseofulvin, for example, are greatly improved when taken in the presence of fatty foods. Pharmacokinetic studies have not been reported to date to evaluate the effect of food on the pharmacokinetics of carisoprodol.

In addition, studies directed to possible negative or competing interactions with other active agents have been limited. While the Carisoma® label lists several drugs whose blood levels may be affected by coadministration with carisoprodol, little information is available that quantifies these effects.

The present invention addresses the need for improved carisoprodol articles and methods of administering carisoprodol.

SUMMARY

There is an especially important need for improvements in carisoprodol articles and methods because the experimentally observed effect of food on the blood levels of this poorly water soluble drug was the opposite of what would normally be expected.

A method of using carisoprodol comprises informing a user that administration of carisoprodol in the presence of food decreases the $C_{max}$ of carisoprodol compared to administration in the absence of food.

A method of using carisoprodol comprises informing a user that administration of carisoprodol in the presence of food decreases the $C_{max}$ of carisoprodol compared to administration in the absence of food, and that an AUC of carisoprodol is substantially unchanged in the presence and absence of food.

A method of using carisoprodol comprises obtaining carisoprodol from a container providing information that administration of carisoprodol in the presence of food decreases the $C_{max}$ of carisoprodol compared to administration in the absence of food.

A method of manufacturing a carisoprodol pharmaceutical composition comprises packaging a carisoprodol pharmaceutical formulation along with information that administration of carisoprodol in the presence of food decreases the $C_{max}$ for carisoprodol compared to administration in the absence of food.

An article of manufacture comprises a container holding a dosage form of carisoprodol, wherein the container is associated with printed labeling instructions advising that administration of carisoprodol in the presence of food decreases the $C_{max}$ of carisoprodol compared to administration in the absence of food.

A method of using carisoprodol comprises informing a user that the carisoprodol should be administered under fasted conditions, on an empty stomach, without food, greater than about 1 hour prior to a meal, at least about 2 hours after consumption of a meal, or a combination of one or more of the foregoing statements.

An article of manufacture comprises a container holding a dosage form suitable for administration of carisoprodol, and printed labeling instructions informing that the carisoprodol should be administered under fasted conditions, on an empty stomach, without food, greater than about 1 hour prior to a meal, at least about 2 hours after consumption of a meal, or a combination comprising one or more of the foregoing statements.

A method of using carisoprodol comprises informing a user that carisoprodol affects activity of cytochrome p450 isozyme CYP2C19; and that administration of carisoprodol with a substance with or without food can affect the plasma concentration, bioavailability, safety, efficacy, or a combination comprising at least one of the foregoing of carisoprodol or the substance.

A method of using carisoprodol comprises informing a user that carisoprodol affects activity of cytochrome p450 isozyme CYP2C19; and that administration of carisoprodol with a narrow therapeutic index drug with or without food can affect the plasma concentration, bioavailability, safety, efficacy, or a combination comprising at least one of the foregoing of carisoprodol or the narrow therapeutic index drug.

A method of using carisoprodol comprises informing a user that during administration of carisoprodol with a substance with or without food, the $T_{max}$ for carisoprodol and the $T_{max}$ for the substance should be considered when determining the timing of administration of the carisoprodol and the substance.

A method of using carisoprodol comprises informing a user that administration of carisoprodol with an active agent that is a CYP2C19, substrate having a narrow therapeutic index can affect plasma concentration, bioavailability, safety, efficacy, or a combination comprising at least one of the foregoing of the active agent, wherein administration is with or without food.

A method of using carisoprodol comprises obtaining carisoprodol from a container providing information that administration of carisoprodol with an active agent that is a CYP2C19 substrate having a narrow therapeutic index can affect plasma concentration, bioavailability, safety, efficacy, or a combination comprising at least one of the foregoing of the active agent, wherein administration is with or without food.

These and other embodiments, advantages and features of the present invention become clear when detailed description and examples are provided in subsequent sections.

DETAILED DESCRIPTION

An "active agent" means a compound, element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound or salt, crystalline forms, non-crystalline forms, and any polymorphs of the compound are contemplated herein. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

"Pharmaceutically acceptable salts" includes derivatives of carisoprodol, wherein the carisoprodol is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues; and the like, and combinations comprising one or more of the foregoing salts. The pharmaceutically acceptable salts include non-toxic salts and the quaternary ammonium salts of the carisoprodol. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, aspharginate, glutamate, and the like; and combinations comprising one or more of the foregoing salts.

"Efficacy" means the ability of an active agent administered to a patient to produce a therapeutic effect in the patient.

"Safety" means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, concomitant medication, or interactions with concomitant medication).

Carisoprodol is a "very sparingly soluble" compound, having a solubility in water of 0.3 to 1.4 mg/mL between 25 to 50° C.

A substance having a "narrow therapeutic index" (NTI) means a substance falling within any definition of narrow therapeutic index as promulgated by the U.S. Food and Drug Administration or any successor agency thereof, for example, a substance having a less than 2-fold difference in median lethal dose (LD50) and median effective dose (ED50) values for the substance, or having a less than 2-fold difference in the minimum toxic concentration and minimum effective concentration in the blood of the substance.

A "dosage form" means a unit of administration of an active agent. Examples of dosage forms include tablets, capsules, injections, suspensions, liquids, emulsions, creams, ointments, suppositories, inhalable forms, transdermal forms, and the like.

By "oral dosage form" is meant to include a unit dosage form for oral administration. An oral dosage form may optionally comprise a plurality of subunits such as, for example, microcapsules or microtablets. Multiple subunits may be packaged for administration in a single dose.

By "subunit" is meant to include a composition, mixture, particle, pellet, etc., that can provide an oral dosage form alone or when combined with other subunits.

A dissolution profile is a plot of the cumulative amount of active agent released as a function of time. A dissolution profile can be measured utilizing the Drug Release Test <724>, which incorporates standard test USP 26 (Test <711>). A profile is characterized by the test conditions selected such as, for example, apparatus type, shaft speed, temperature, volume, and pH of the dissolution medium. More than one dissolution profile may be measured. For example, a first dissolution profile can be measured at a pH level approximating that of the stomach, and a second dissolution profile can be measured at a pH level approximating that of one point in the intestine or several pH levels approximating multiple points in the intestine.

A highly acidic pH may be employed to simulate the stomach and a less acidic to basic pH may be employed to simulate the intestine. By the term "highly acidic pH" is meant a pH of about 1 to about 4. A pH of about 1.2, for example, can be used to simulate the pH of the stomach. By the term "less acidic to basic pH" is meant a pH of greater than about 4 to about 7.5, specifically about 6 to about 7.5. A pH of about 6 to about 7.5, specifically about 6.8, can be used to simulate the pH of the intestine.

By "immediate-release" is meant a conventional or non-modified release in which greater then or equal to about 75% of the active agent is released within two hours of administration, specifically within one hour of administration.

By "controlled-release" is meant a dosage form in which the release of the active agent is controlled or modified over a period of time. Controlled can mean, for example, sustained-, delayed- or pulsed-release at a particular time. Alternatively, controlled can mean that the release of the active agent is extended for longer than it would be in an immediate-release dosage form, e.g., at least over several hours.

Dosage forms can be combination dosage forms having both immediate-release and controlled-release characteristics, for example, a combination of immediate-release pellets and controlled-release pellets. The immediate-release portion of a combination dosage form may be referred to as a loading dose.

"Bioavailability" means the extent or rate at which an active agent is absorbed into a living system or is made available at the site of physiological activity. For active agents that are intended to be absorbed into the bloodstream, bioavailability data for a given formulation may provide an estimate of the relative fraction of the administered dose that is absorbed into the systemic circulation. "Bioavailability" can be characterized by one or more pharmacokinetic parameters.

"Pharmacokinetic parameters" describe the in vivo characteristics of an active agent (or surrogate marker for the active agent) over time, such as plasma concentration (C), $C_{max}$, $C_n$, $C_{24}$, $T_{max}$, and AUC. "$C_{max}$" is the measured concentration of the active agent in the plasma at the point of maximum concentration. "$C_n$" is the measured concentration of an active agent in the plasma at about n hours after administration. "$C_{24}$" is the measured concentration of an active agent in the plasma at about 24 hours after administration. The term "$T_{max}$" refers to the time at which the measured concentration of an active agent in the plasma is the highest after administration of the active agent. "AUC" is the area under the curve of a graph of the measured concentration of an active agent (typically plasma concentration) vs. time, measured from one time point to another time point. For example $AUC_{0-t}$ is the area under the curve of plasma concentration versus time from time 0 to time t. The $AUC_{0-\infty}$ or $AUC_{0-INF}$ is the calculated area under the curve of plasma concentration versus time from time 0 to time infinity.

Bioequivalent means a product or method falling within a definition of bioequivalent as promulgated by the U.S. Food and Drug Administration or any successor agency thereof. Under current U.S. FDA guidelines, two products or methods (e.g., dosing under non-fasted versus fasted conditions) are bioequivalent if the 90% Confidence Intervals (CI) for a log transformed geometric mean of $AUC_{0-INF}$ and $C_{max}$ are 0.80 to 1.25 ($T_{max}$ measurements are not relevant to bioequivalence for regulatory purposes). To show bioequivalency between two compounds or administration conditions pursuant to Europe's EMEA guidelines, the 90% CI for a log transformed geometric mean of $AUC_{0-INF}$, must be 0.80 to 1.25 and the 90% CI for a log transformed geometric mean of $C_{max}$ must be 0.70 to 1.43.

Information as disclosed herein may include information that two administration methods are bioequivalent under FDA guidelines, are substantially bioequivalent, or have insignificant differences in their pharmacokinetic parameters.

Certain formulations described herein may be "coated". The coating may be a suitable coating, such as, a functional or a non-functional coating, or multiple functional and/or non-functional coatings. By "functional coating" is meant to include a coating that modifies the release properties of the total formulation, for example, a sustained-release coating. By "non-functional coating" is meant to include a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition.

"Informing" means referring to or providing, published material, for example, providing an active agent with published material to a user; or presenting information orally, for example, by presentation at a seminar, conference, or other educational presentation, by conversation between a pharmaceutical sales representative and a medical care worker, or by conversation between a medical care worker and a patient; or demonstrating the intended information to a user for the purpose of comprehension.

A "medical care worker" means a worker in the health care field who may need or utilize information regarding an active agent including a dosage form thereof, including information on safety, efficacy, dosing, administration, or pharmacokinetics. Examples of medical workers include physicians, pharmacists, physician's assistants, nurses, aides, caretakers (which can include family members or guardians), emergency medical workers, and veterinarians.

A "patient" means a human or non-human animal in need of medical treatment. Medical treatment can include treatment of an existing condition, such as a disease or disorder, prophylactic or preventative treatment, or diagnostic treatment. In some embodiments the patient is a human patient.

A "pharmaceutical supplier" means a person (other than a medical care worker), business, charitable organization, governmental organization, or other entity involved in the transfer of active agent, including a dosage form thereof, between entities, for profit or not. Examples of pharmaceutical suppliers include pharmaceutical distributors, pharmacy chains, pharmacies (online or physical), hospitals, HMOs, supermarkets, the Veterans Administration, or foreign businesses or individuals importing active agent into the United States.

A "user" means a patient, a medical care worker, or a pharmaceutical supplier.

A "product" or "pharmaceutical product" means a dosage form of an active agent plus published material and optionally packaging.

"Providing" means giving, administering, selling, distributing, transferring (for profit or not), manufacturing, compounding, or dispensing.

"Published material" means a medium providing information, including printed, audio, visual, or electronic medium, for example a flyer, an advertisement, a product insert, printed labeling, an internet web site, an internet web page, an internet pop-up window, a radio or television broadcast, a compact disk, a DVD, an audio recording, or other recording or electronic medium.

Food typically means a solid food or mixed solid/liquid food with sufficient bulk and fat content that it is not rapidly dissolved and absorbed in the stomach. In one embodiment, food means a meal, such as breakfast, lunch or dinner. The terms "taken with food", "fed" and "non-fasted" are equivalent and are as given by FDA guidelines and criteria. In one embodiment, with food means that the dosage form is administered to a patient between about 30 minutes prior to about 2 hours after eating a meal. In another embodiment, with food means that the dosage form is administered at substantially the same time as the eating the meal.

The terms "without food", "fasted" and "an empty stomach" are equivalent and are as given by FDA guidelines and criteria. In one embodiment, fasted is means the condition wherein no food is consumed within 1 hour prior to administration of the dosage form or 2 hours after administration of the dosage form. In another embodiment, fasted means the condition wherein no food is consumed within 1 hour prior to administration of the dosage form to 2 hours after administration of the dosage form.

Carisoprodol is a sparingly water soluble and lipophilic drug, and as such, it may be expected that administration of carisoprodol in the presence of a high fat meal will increase its bioavailability. Food can affect gastric emptying, and may also alter the release of a drug from a dosage form, the solubilization of the drug, and the transport of the drug across the intestinal wall. For lipophilic, sparingly water soluble drugs, fatty meals can increase gastric residence time thereby increasing the time available for solubilization and also may enhance the solubilization of the drug by the lipids contained in the meal. Studies were thus undertaken to determine if administration of carisoprodol in the presence and absence of food has an effect on its pharmacokinetic parameters or those of its metabolite, meprobamate.

Unexpectedly, administration of carisoprodol in the presence of food decreases the $C_{max}$ for carisoprodol compared to administration in the absence of food. In one embodiment, administration of carisoprodol in the presence of food (non-fasted) results in a 16% decrease in the geometric mean of $C_{max}$ for carisoprodol compared to administration in the absence of food (fasted). Also unexpectedly, while the $C_{max}$ for carisoprodol decreases in the presence of food, the $AUC_{0-t}$ and $AUC_{0-INF}$ for carisoprodol remain substantially unchanged. In one embodiment, according to current FDA criteria, by substantially unchanged, it is meant that there is a 90% Confidence Interval of 0.80 to 1.25 for the ratio of the ln transformed geometric mean of a pharmacokinetic parameter (e.g., AUC) for the non-fasted state compared to the fasted state. In one embodiment, the geometric mean of $AUC_{0-t}$ and $AUC_{0-INF}$ for carisoprodol remain substantially unchanged in the presence and absence of food. In other words, the 90% confidence interval for the ratio of the geometric means between the non-fasted and fasted states is within the interval of 80-125% for 1n-transformed $AUC_{0-t}$ and $AUC_{0-INF}$.

In addition to the pharmacokinetic parameters for carisoprodol, the pharmacokinetic parameters for meprobamate as a metabolite of carisoprodol were determined. In contrast to carisoprodol, the $C_{max}$ and AUC (e.g., $AUC_{0-t}$ and $AUC_{0-INF}$) for meprobamate as a metabolite of carisoprodol are both substantially unchanged in the presence and absence of food. That is, there is a 90% Confidence Interval of 0.80 to 1.25 for the ratio of the ln transformed geometric mean of AUC (e.g., $AUC_{0-t}$ and $AUC_{0-INF}$) and $C_{max}$ for meprobamate as a metabolite of carisoprodol in the non-fasted state compared to the fasted state. In other words, the 90% confidence interval for the ratio of the geometric means between the non-fasted and fasted states is within the interval of 80-125% for 1n-transformed $C_{max}$, $AUC_{0-t}$ and $AUC_{0-INF}$.

A method of using carisoprodol comprises informing a user that administration of carisoprodol in the presence of food results in a decrease in the $C_{max}$ for carisoprodol compared to administration in the absence of food. A method of using carisoprodol comprises informing a user that administration of carisoprodol in the presence and absence of food has no significant effect on the AUC (e.g., $AUC_{0-t}$ and $AUC_{0-INF}$) for carisoprodol. In another embodiment, a method of using carisoprodol comprises informing a user that administration of carisoprodol is substantially bioequivalent in the presence and absence of food. In one embodiment, the method further comprises informing a user that administration of carisoprodol in the presence or absence of food has no significant effect on the $C_{max}$ and AUC (e.g., $AUC_{0-t}$ and $AUC_{0-INF}$) for meprobamate as a metabolite of carisoprodol. The method may also include providing a patient in need of carisoprodol with a pharmaceutical formulation comprising a therapeutically effective amount of carisoprodol.

In another embodiment, a method of using carisoprodol comprises informing a user that administration of carisoprodol in the presence of food decreases the $C_{max}$ of carisoprodol compared to administration in the absence of food, and that the AUC of carisoprodol is substantially unchanged in the presence and absence of food.

In another embodiment, a method of using carisoprodol comprises providing a user with a pharmaceutical formulation comprising a therapeutically effective amount of carisoprodol, and informing the patent that administration of carisoprodol in the presence of food results in a decrease in the $C_{max}$ for carisoprodol compared to administration in the absence of food.

In yet another embodiment, a method of using carisoprodol comprises obtaining carisoprodol from a container providing information that administration of carisoprodol in the presence of food decreases the $C_{max}$ of carisoprodol compared to administration in the absence of food.

An article of manufacture comprises a container holding a dosage form suitable for administration of carisoprodol, and printed labeling instructions providing a discussion that administration of carisoprodol in the presence of food decreases the $C_{max}$ for carisoprodol compared to administration in the absence of food. In addition, or alternatively, the printed labeling instructions inform that the carisoprodol should be administered under fasted conditions, on an empty stomach, without food, greater than about 1 hour prior to a meal, at least about 2 hours after consumption of a meal, or a combination comprising one or more of the foregoing statements.

A method of manufacturing a carisoprodol pharmaceutical composition comprises packaging a carisoprodol pharmaceutical formulation along with information that administration of carisoprodol in the presence of food decreases the $C_{max}$ for carisoprodol compared to administration in the absence of food. In addition, or alternatively, the information advises that the carisoprodol should be administered under fasted conditions, on an empty stomach, without food, greater than about 1 hour prior to a meal, at least about 2 hours after consumption of a meal, or a combination comprising one or more of the foregoing statements.

The dosage form will typically be contained in a suitable container capable of holding and dispensing the dosage form and which will not significantly interact with the composition and will further be in physical relation with the appropriate labeling advising that the carisoprodol formulation may be taken with or without food. The labeling may be associated with the container by a means that maintains a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

In the foregoing embodiments, informing is by reference to published material; by reference to a package active agent insert, a flyer or an advertisement; by presentation of information at a seminar, conference, or other educational presentation; or by a conversation between a pharmaceutical sales representative and the medical care worker.

In the foregoing embodiments, informing/information includes providing a discussion that administration of carisoprodol in the presence of food results in a decrease in the $C_{max}$ for carisoprodol compared to administration in the absence of food. The informing/information may include a statement that administration of carisoprodol in the presence of food results in a 16% decrease in the geometric mean of $C_{max}$ for carisoprodol compared to administration in the absence of food. In addition to, or alternatively, the informing/information may include a statement that in a study of 22 patients, the geometric mean Of $C_{max}$ for carisoprodol when administered under non-fasted conditions was 1680 ng/ml, and the geometric mean of $C_{max}$ for carisoprodol when administered under fasted conditions was 2003 ng/ml.

The informing/information may further provide a discussion that the AUC (e.g., $AUC_{0-t}$ or $AUC_{0-INF}$) for carisoprodol is substantially unchanged in the presence and absence of food. The informing/information may include a statement that administration of carisoprodol in the presence of food results in substantially no difference in $AUC_{0-t}$ or $AUC_{0-INF}$ for carisoprodol. In one embodiment, informing provides a discussion that the 90% confidence interval for the ratio of the geometric means between the non-fasted and fasted states for carisoprodol is within the interval of 80-125% for ln-transformed $AUC_{0-t}$ and $AUC_{0-INF}$. In one embodiment, the informing/information may provide a discussion that in a study of 22 patients, the geometric mean of $AUC_{0-t}$ for carisoprodol was 6136 hr*ng/ml when administered under non-fasted conditions and 6385 hr*ng/ml when administered under fasted conditions. In one embodiment, the informing/ information may provide a discussion that in a study of 22 patients, the geometric mean of $AUC_{0-INF}$ for carisoprodol was 6306 hr*ng/ml when administered under non-fasted conditions and 6512 hr*ng/ml when administered under fasted conditions.

The informing/information may further include a statement that administration of carisoprodol in the presence of food has no significant effect on the $C_{max}$ or AUC (e.g., $AUC_{0-t}$ or $AUC_{0-INF}$) for meprobamate as a metabolite of carisoprodol. The informing/information may advise that the 90% confidence interval for the ratio of the geometric means between the non-fasted and fasted states for meprobamate as a metabolite of carisoprodol is within the interval of 80-125% for in-transformed AUC or $C_{max}$. In addition to, or alternatively, the informing/information may include a statement that in a study of 22 patients, the geometric mean of $C_{max}$ for meprobamate as a metabolite of carisoprodol administered under non-fasted conditions was 2352 ng/ml, and the geometric mean of $C_{max}$ for meprobamate as a metabolite of carisoprodol administered under fasted conditions was 2280 ng/ml. In one embodiment, the informing/information may provide a discussion that in a study of 22 patients, the geometric mean of $AUC_{0-t}$ for meprobamate was 30745 hr*ng/ml as a metabolite of carisoprodol administered under non-fasted conditions and 30412 hr*ng/ml as a metabolite of carisoprodol administered under fasted conditions. In one embodiment, the informing/information may provide a discussion that in a study of 22 patients, the geometric mean of $AUC_{0-INF}$ for meprobamate was 37942 hr*ng/ml as a metabolite of carisoprodol administered under non-fasted conditions and 38005 hr*ng/ml as a metabolite of carisoprodol administered under fasted conditions.

In another aspect, a method of using carisoprodol comprises informing a user that carisoprodol affects the activity of cytochrome p450 isozyme CYP2C19; and that administration of carisoprodol with a substance with or without food can affect the plasma concentration, bioavailability, safety, efficacy, or a combination comprising at least one of the foregoing of carisoprodol or the substance.

In one embodiment, co-administration of carisoprodol with a second drug that is metabolized by a cytochrome p450 isoform that metabolizes carisoprodol, e.g., cytochrome CYP2C19, can affect the metabolism of the carisoprodol, the second drug, or both when taken with or without food. In one embodiment, the second drug comprises a narrow therapeutic index drug such as, for example, phenytoin or warfarin. Enzymes involved in drug metabolism such as cytochrome p450s respond to the constantly changing amounts of substrate drugs they encounter. Administration of a substrate drug in the presence of food can alter the amount of substrate drug available to the enzymes. Changes in drug metabolism due to competition variability caused by food with the same cytochrome p450 isoform may change a clinical characteristic, e.g., the blood levels, of a drug. In the case of a narrow therapeutic index drug, too little drug can lead to insufficient therapeutic activity, while too large of a dose can lead to excessive activity, both of which can be detrimental. In particular, co-administration of carisoprodol and a narrow therapeutic index drug with or without food can lead to variable blood levels of the carisoprodol, the narrow therapeutic index drug, or both.

A method of treatment comprises administering to a patient in need of both carisoprodol and a second drug, a therapeutically effective amount of both carisoprodol and the second drug, wherein the second drug is a narrow therapeutic index drug which is metabolized by cytochrome p450 isoform CYP2C19, regularly monitoring the blood levels of the narrow therapeutic index drug as $AUC_{0-INF}$, $C_{MAX}$, or a combination comprising one or more of the foregoing pharmacokinetic parameters, and informing the patient that the amount bioavailability of the second drug may be affected by the presence of food.

A method of using carisoprodol comprises informing a user that during administration of carisoprodol with a substance with or without food, the $T_{max}$ for carisoprodol and the substance should be considered when determining the timing of administration of the carisoprodol and the substance. The substance comprises, for example, a narrow therapeutic index drug. The method may also comprise informing that administration of the carisoprodol and the narrow therapeutic index drug should be timed so that the $C_{max}$ for carisoprodol and the $C_{max}$ for the narrow therapeutic index drug do not occur at similar times, or occur at the most dissimilar times that can be achieved.

A method of treatment comprises administering to a patient in need of both carisoprodol and a second drug, a therapeutically effective amount of both carisoprodol and the second drug, wherein the second drug is a narrow therapeutic index drug which is metabolized by cytochrome p450 isoform CYP2C19, and informing the patient that carisoprodol, the second drug, or both, should be taken consistently with food or consistently without food. Administration consistently with or without food can reduce changes in a blood level of the carisoprodol, the substance, or both.

A method of treatment comprises administering to a patient in need of both carisoprodol and a second drug, a therapeutically effective amount of both carisoprodol and the second drug, wherein the second drug is a narrow therapeutic index drug which is metabolized by cytochrome p450 isoform CYP2C19, and informing the patient that carisoprodol, the second drug, or both, should be taken on an empty stomach, under fasted conditions, without food, greater than about 1 hour prior to a meal, at least about 2 hours after consumption of a meal, or a combination comprising one or more of the foregoing statements.

A method of treatment comprises administering to a patient in need of both carisoprodol and a second drug, a therapeutically effective amount of both carisoprodol and the second drug, wherein the second drug is a narrow therapeutic index drug which is metabolized by cytochrome p450 isoform CYP2C19, and informing the patient that carisoprodol, the second drug, or both, should be taken on a full stomach, under fed conditions, with food, within 30 minutes prior to a meal, within 2 hours after a meal, or a combination comprising one or more of the foregoing statements.

Solid dosage forms for oral administration include, but are not limited to, capsules, tablets, pills, powders, and granules. In such solid dosage forms, the active agent may be admixed with one or more of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, and combinations comprising one or more of the foregoing additives. For capsules, tablets, and pills, the dosage forms optionally comprise buffering agents.

The dosage forms described herein are optionally coated with a functional or non-functional coating. The coating comprises about 0 wt % to about 40 wt % of the composition. Suitable coating materials include a polymer, such as a film-forming polymer including, for example, methyl cellulose, ethyl cellulose, hydroxypropyl cellulose, hydroxypropyl methyl cellulose, hydroxybutyl methyl cellulose, cellulose acetate, cellulose propionate, cellulose acetate propionate, cellulose acetate butyrate, cellulose acetate phthalate, carboxymethyl cellulose, cellulose triacetate, cellulose sulphate sodium salt, poly(methyl methacrylate), poly (ethyl methacrylate), poly (butyl methacrylate), poly (isobutyl methacrylate), poly (hexyl methacrylate), poly (phenyl methacrylate), poly (methyl acrylate), poly (isopropyl acrylate), poly (isobutyl acrylate), poly (octadecyl acrylate), poly (ethylene), poly (ethylene) low density, poly (ethylene)high density, (poly propylene), poly (ethylene glycol poly (ethylene oxide), poly (ethylene terephthalate), poly(vinyl alcohol), poly(vinyl isobutyl ether), poly(viny acetate), poly (vinyl chloride), polyvinyl pyrrolidone, and combinations comprising one or more of the foregoing polymers.

In some applications, the polymer is a water-insoluble polymer. Water insoluble polymers include ethyl cellulose or dispersions of ethyl cellulose, acrylic and/or methacrylic ester polymers, cellulose acetates, butyrates or propionates or copolymers of acrylates or methacrylates having, for example, a low quaternary ammonium content, and the like, and combinations comprising one or more of the foregoing polymers.

In some controlled-release applications, for example, the coating is a hydrophobic polymer that modifies the release properties of the API from the formulation. Suitable hydrophobic or water insoluble polymers for controlled-release include, for example, methacrylic acid esters, ethyl cellulose, cellulose acetate, polyvinyl alcohol-maleic anhydride copolymers, β-pinene polymers, glyceryl esters of wood resins, and combinations comprising one or more of the foregoing polymers.

The inclusion of an effective amount of a plasticizer in the coating composition may improve the physical properties of the film. For example, because ethyl cellulose has a relatively high glass transition temperature and does not form flexible films under normal coating conditions, it may be advantageous to add plasticizer to the ethyl cellulose before using the same as a coating material. Generally, the amount of plasticizer included in a coating solution is based on the concentration of the polymer, e.g., most often from about 1 wt % to about 50 wt % of the polymer. Concentrations of the plasticizer, however, can be determined by routine experimentation.

Examples of plasticizers for ethyl cellulose and other celluloses include plasticizers such as dibutyl sebacate, diethyl phthalate, triethyl citrate, tributyl citrate, triacetin, and combinations comprising one or more of the foregoing plasticizers, although it is possible that other water-insoluble plasticizers (such as acetylated monoglycerides, phthalate esters, castor oil, etc.) can be used.

Examples of plasticizers for acrylic polymers include citric acid esters such as triethyl citrate NF, tributyl citrate, dibutyl phthalate, 1,2-propylene glycol, polyethylene glycols, propylene glycol, diethyl phthalate, castor oil, triacetin, and combinations comprising one or more of the foregoing plasticizers, although it is possible that other plasticizers (such as acetylated monoglycerides, phthalate esters, castor oil, etc.) can be used.

In certain embodiments, it is preferred that the coating is a substantially continuous coat and substantially hole-free. By substantially continuous coating is meant a coating which retains a smooth and continuous appearance when magnified 1000 times under a scanning electron microscope and wherein no holes or breakage of the coating are evident.

Suitable methods can be used to apply the coating to the dosage form. Processes such as simple or complex coacervation, interfacial polymerization, liquid drying, thermal and ionic gelation, spray drying, spray chilling, fluidized bed coating, pan coating, or electrostatic deposition, may be used. A substantially continuous nature of the coating may be achieved, for example, by spray drying from a suspension or dispersion of the coating composition.

The coating, if present, are about 0.005 micrometers to about 25 micrometers thick, preferably about 0.05 micrometers to about 5 micrometers.

In one embodiment, a carisoprodol dosage form is an oral dosage form such as, for example, a tablet. Oral dosage forms comprise about 100 mg to about 1000 mg of carisoprodol, specifically about 200 to about 400 mg of carisoprodol, and more specifically about 350 mg of carisoprodol. In one embodiment, the oral dosage form is an immediate-release oral dosage form.

EXAMPLES

Example 1

Study of Carisoprodol Pharmacokinetics Under Non-fasted and Fasted Conditions

A biostudy was conducted under fasted and non-fasted conditions.

As used herein, for the purposes of biostudy and the determination of bioequivalence, a fasted patient is defined as a patient who does not eat any food, i.e., fasts for at least 10 hours before the administration of a dosage form of carisoprodol and who does not eat any food and continues to fast for at least 4 hours after the administration of the dosage form. The dosage form is administered with 240 ml of water during the fasting period, and water can be allowed ad libitum after 2 hours.

As used herein, for the purposes of biostudy and the determination of bioequivalence, a non-fasted patient is defined as a patient who fasts for at least 10 hours overnight and then consumes an entire test meal within 30 minutes of first ingestion. The dosage form is administered with 240 mL of water at 30 minutes after first ingestion of the meal. No food is then allowed for at least 4 hours post-dose. Water can be allowed ad libitum after 2 hours. A high fat test meal provides approximately 1000 calories to the patient of which approximately 50% of the caloric content is derived from fat content of the meal. A representative high fat high calorie test meal comprises 2 eggs fried in butter, 2 strips of bacon, 2 slices of toast with butter, 4 ounces of hash brown potatoes, and 8 ounces of whole milk to provide 150 protein calories, 250 carbohydrate calories, and 500 to 600 fat calories.

The study was designed as a randomized, single-dose two-way crossover to compare the pharmacokinetic parameters of SOMA®. Twenty-four healthy adults participated in this comparison study and 22 of the subjects completed the study. Subjects received two separate drug administration treatments in assigned periods, one treatment per period, according to the randomization schedule. Dosing days were separated by a washout period of at least seven days. Blood samples were drawn prior to dosing (pre-dose) and at 0.33, 0.67, 1, 1.5, 2, 2.5, 3, 3.5, 4, 5, 6, 7, 8, 10, 12, 18, and 24 hours post-dose. The samples were then analyzed for carisoprodol and meprobamate.

The following pharmacokinetic parameters may be determined from the plasma concentration data:

The area under the plasma concentration versus time curve [$AUC_t$] may be calculated using the linear trapezoidal rule from the zero time point to the last measured concentration.

The area under the plasma concentration versus time curve from zero to infinity [$AUC_{0-INF}$] may be calculated by adding $C_t/K_{elm}$ to AUC where $C_t$ is the last measured concentration and $K_{elm}$ is the elimination rate constant.

The maximum observed plasma concentration [$C_{max}$] may be obtained by inspection. The $C_{max}$ may also be designated as $C_{MAX}$.

The time to maximum plasma concentration [$T_{max}$] may be obtained by inspection. If the same maximum plasma concentration occurs at more than one time point, the first may be chosen as $T_{max}$.

The terminal elimination rate constant [$K_{elm}$] may be obtained from the slope of the line, fitted by linear least squares regression, through the terminal points of the ln(base e) of the concentration versus time plot for these points.

The half-life [$T_{1/2}$] may be calculated by the equation $T_{1/2} = 0.693/K_{elm}$.

The data for carisoprodol is shown in Tables 1 and 2:

TABLE 1

Ln-transformed pharmacokinetic parameters for carisoprodol

|  | Non-Fasted, Geometric Mean | Fasted, Geometric Mean | % Ratio | 90% Confidence Interval (Lower limit, upper limit) |
|---|---|---|---|---|
| $C_{max}$ (ng/ml) | 1680 | 2003 | 83.8 | (73.72, 95.36) |
| $AUC_{0-t}$ (hr*ng/ml) | 6136 | 6385 | 96.1 | (90.99, 101.51) |
| $AUC_{0-INF}$ (hr*ng/ml) | 6306 | 6512 | 96.8 | (91.8, 102.14) |

TABLE 2

Non-transformed pharmacokinetic parameters for carisoprodol

|  | Non-Fasted, Least Sq. Mean | Fasted, Least Sq. Mean | % Ratio |
|---|---|---|---|
| $T_{max}$ (hr) | 2.24 | 1.63 | 137.5 |
| $k_{elm}$ | 0.3713 | 0.376 | 98.7 |
| $T_{1/2}$ (hr) | 1.95 | 1.95 | 100 |

The data for meprobamate, as a metabolite of carisoprodol, is shown in Tables 3 and 4:

TABLE 3

Ln-transformed pharmacokinetic parameters for meprobamate as a metabolite of carisoprodol

|  | Non-Fasted, Geometric Mean | Fasted, Geometric Mean | % Ratio | 90% Confidence Interval (Lower limit, upper limit) |
|---|---|---|---|---|
| $C_{max}$ (ng/ml) | 2352 | 2280 | 103.1 | (100.8, 105.5) |
| $AUC_{0-t}$ (hr*ng/ml) | 30745 | 30412 | 101.1 | (99.4, 102.8) |
| $AUC_{0-INF}$ (hr*ng/ml) | 37942 | 38005 | 99.8 | (97.7, 102.0) |

TABLE 4

Non-transformed pharmacokinetic parameters for meprobamat as a metabolite of carisoprodol

|  | Non-Fasted, Least Sq. Mean | Fasted, Least Sq. Mean | % Ratio |
|---|---|---|---|
| $T_{max}$ (hr) | 4.57 | 3.82 | 119.6 |
| $k_{elm}$ | 0.0796 | 0.0753 | 105.6 |
| $T_{1/2}$ (hr) | 8.93 | 9.44 | 94.6 |

The conclusion from these data is that administration under non-fasted (i.e., fed) conditions decreases the $C_{max}$ of carisoprodol compared to administration under fasted conditions, however, the AUC of carisoprodol is substantially unchanged when administered in non-fasted compared to fasted conditions. In addition, the pharmacokinetic profile of meprobamate as a metabolite of carisoprodol is substantially unchanged when carisoprodol was administered under non-fasted compared to fasted conditions.

The terms "a" and "an" do not denote a limitation of quantity, but rather denote the presence of at least one of the referenced item.

The term "or" means "and/or".

The terms "comprising", "having", "including", and "containing" are to be construed as open-ended terms (i.e., meaning "including, but not limited to").

The endpoints of all ranges directed to the same component or property are inclusive and independently combinable.

Unless defined otherwise, technical and scientific terms used herein have the same meaning as is commonly understood by one of skill in the art to which this invention belongs.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method of decreasing the peak plasma concentration of carisoprodol experienced by a patient, comprising:
   administering a carisoprodol dosage form to a human patient in need thereof with food, wherein peak plasma concentration ($C_{max}$) of carisoprodol is less than $C_{max}$ of carisoprodol after administration of the carisoprodol dosage form without food.

2. The method of claim 1, wherein in a study of 22 subjects, administration of the carisoprodol dosage form with food results in a 16% decreases in a geometric mean $C_{max}$ of carisoprodol compared to a geometric mean $C_{max}$ of carisoprodol after administration of the carisoprodol dosage form without food.

3. The method of claim 1, wherein in a study of 22 subjects, the geometric mean of $C_{max}$ for the carisoprodol dosage form when administered under non-fasted conditions was 1680 ng/ml, and the geometric mean of $C_{max}$ for the carisoprodol dosage form when administered under fasted conditions was 2003 ng/ml.

4. The method of claim 1, wherein administration of the carisoprodol dosage form with or without food has no significant effect on $C_{max}$ or area under the plasma concentration curve (AUC) of meprobamate resulting from metabolism of carisoprodol.

5. The method of claim 1, wherein the carisoprodol dosage form is an oral dosage form.

6. The method of claim 5, wherein the oral dosage form is a tablet and the tablet comprises about 100 to about 1000 mg of carisoprodol.

7. A method of administering carisoprodol to a human patient comprising:
   administering carisoprodol and a substrate of cytochrome p450 isozyme CYP2C19 having a narrow therapeutic index to a human patient in need thereof, wherein the carisoprodol is administered to the patient with food.

8. The method of claim 7, further comprising:
   monitoring the blood levels of the substrate for changes in metabolism of the substrate.

9. The method of claim 1: further comprising
   timing administration of carisoprodol and administration of the substrate such that the $T_{max}$ for carisoprodol and the $T_{max}$ for the substrate occur at the most dissimilar times that can be achieved.

10. The method of claim 1 wherein the patient is in need of a skeletal muscle relaxant.

11. The method of claim 7 wherein the patient is in need of a skeletal muscle relaxant.

* * * * *